United States Patent [19]
Bhinde et al.

[11] Patent Number: 5,550,301
[45] Date of Patent: *Aug. 27, 1996

[54] DRIED CATALYTIC SYSTEMS FOR DECOMPOSITION OF ORGANIC HYDROPEROXIDES

[75] Inventors: Manoj V. Bhinde, Boothwyn; James E. Lyons, Wallingford; Paul E. Ellis, Jr., Downingtown, all of Pa.

[73] Assignee: Sun Company, Inc. (R&M), Philadelphia, Pa.

[*] Notice: The term of this patent shall not extend beyond the expiration date of Pat. No. 5,395,988.

[21] Appl. No.: 398,024

[22] Filed: Mar. 3, 1995

Related U.S. Application Data

[63] Continuation-in-part of Ser. No. 223,090, Apr. 4, 1994, Pat. No. 5,395,988.

[51] Int. Cl.$^6$ ............ C07C 29/00; C07C 31/12; C07C 33/22; C07C 35/14
[52] U.S. Cl. ............ 568/835; 568/798; 568/815; 568/909.8
[58] Field of Search ............ 568/909.8, 835, 568/815, 798

[56] References Cited

U.S. PATENT DOCUMENTS

| | | |
|---|---|---|
| 4,551,553 | 11/1985 | Taylor et al. . |
| 4,912,266 | 3/1990 | Sanderson et al. . |
| 4,912,267 | 3/1990 | Sanderson et al. . |
| 4,922,035 | 5/1990 | Sanderon et al. . |
| 4,922,036 | 5/1990 | Sanderson et al. . |
| 4,992,602 | 2/1991 | Sanderson et al. . |
| 5,120,886 | 6/1992 | Lyons et al. . |
| 5,395,988 | 3/1995 | Bhinde et al. ............ 568/909.8 |

*Primary Examiner*—Joseph E. Evans
*Attorney, Agent, or Firm*—Todd Q. Dickinson; Stephen T. Falk

[57] ABSTRACT

Organic hydroperoxides are decomposed by drying a reaction mixture containing the organic hydroperoxide and an organic solvent such that said dried reaction mixture comprises approximately 1 weight percent or less of water and contacting the dried reaction mixture with a metal organic ligand catalyst under hydroperoxide decomposition conditions. An organic co-solvent for the hydroperoxide may also be used. Particularly effective catalysts are cobalt acetylacetonates and ruthenium acetylacetonates and combinations thereof.

37 Claims, 6 Drawing Sheets

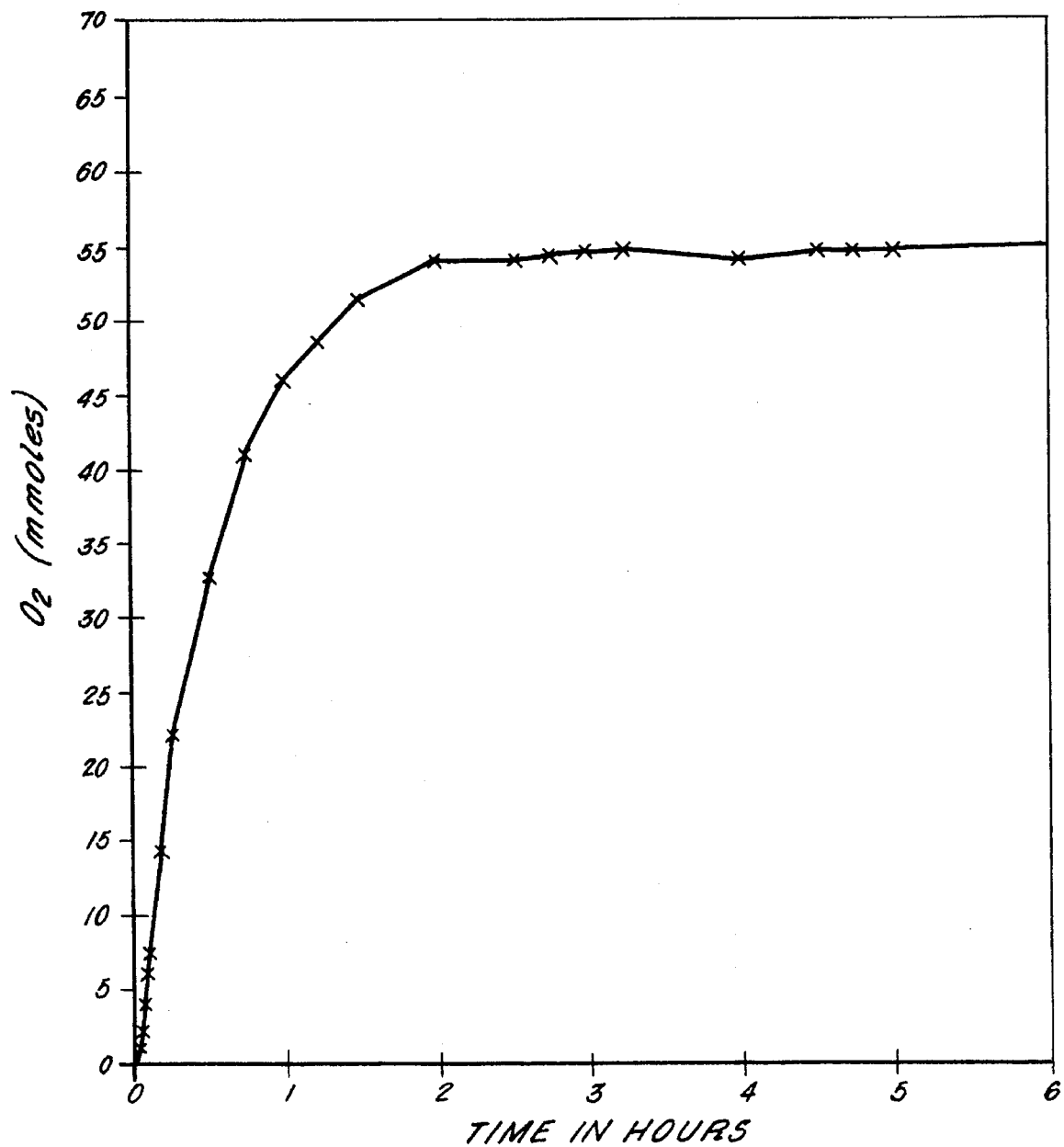

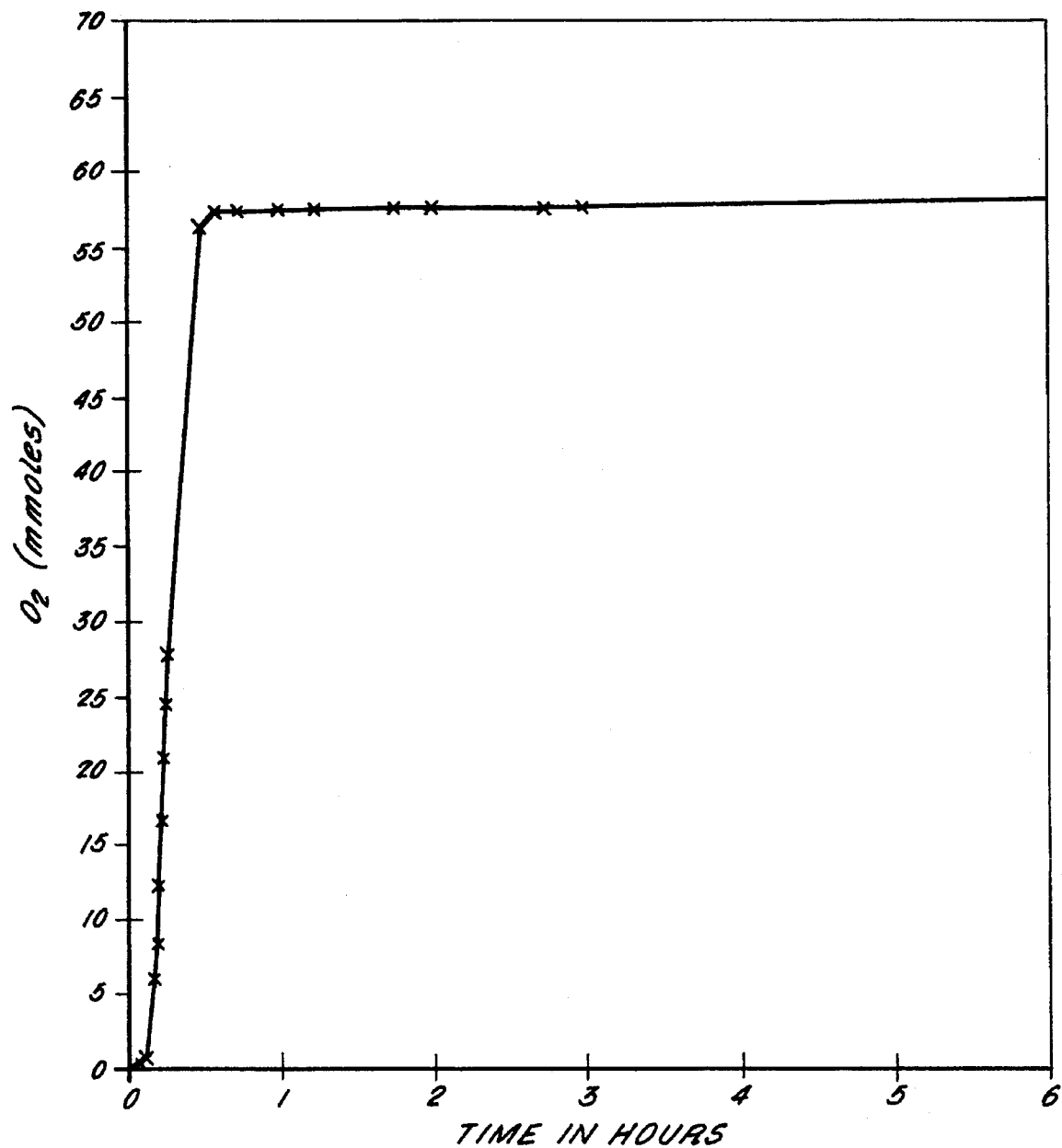

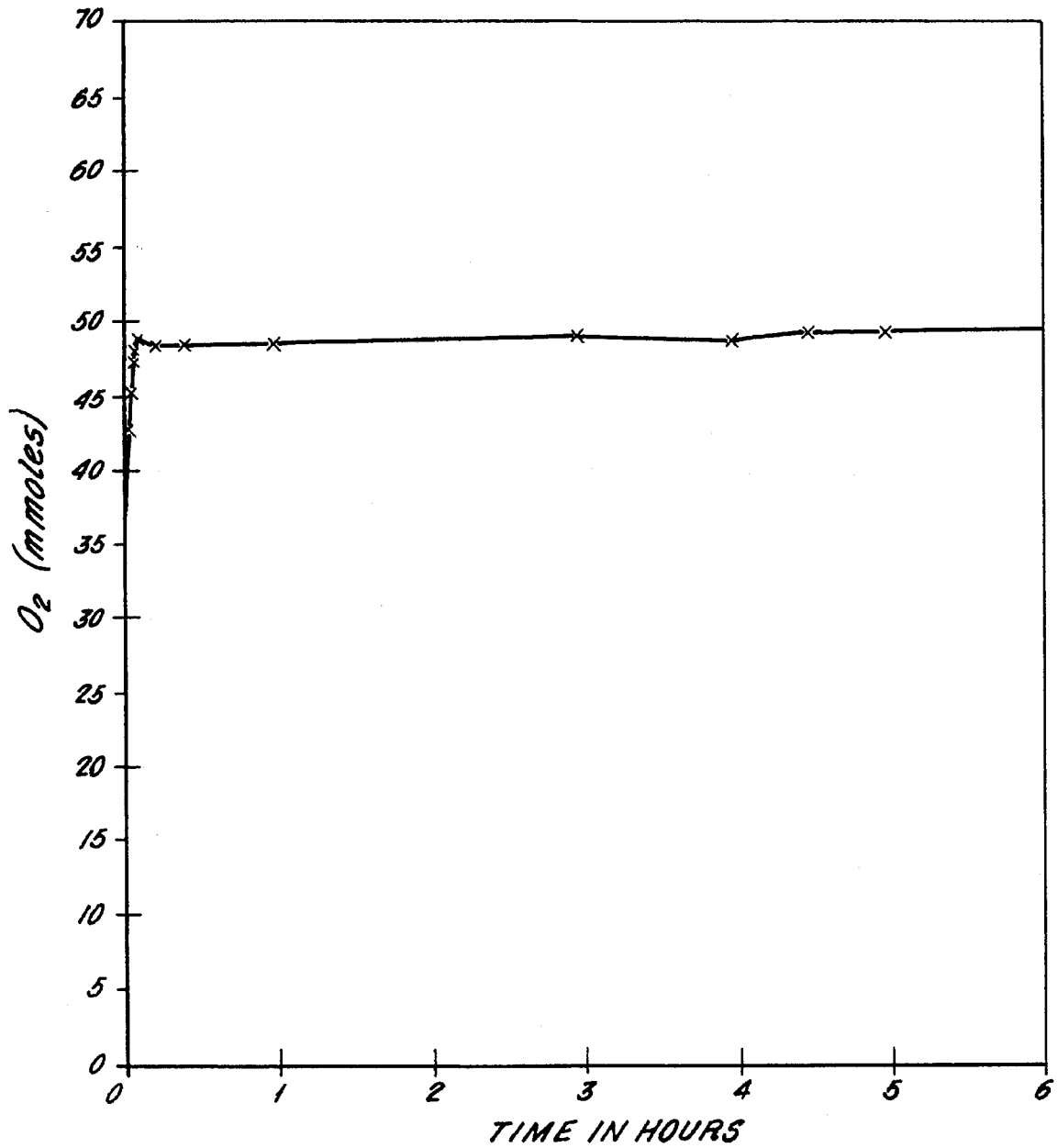

DRIED CATALYTIC SYSTEMS FOR DECOMPOSITION OF ORGANIC HYDROPEROXIDES

This application is a continuation-in-part of application Ser. No. 08/223,090, filed Apr. 4, 1994, now U.S. Pat. No. 5,395,988.

BACKGROUND

Metallophthalocyanine complexes are known catalysts for the decomposition of hydroperoxides. Sanderson et al., U.S. Pat. Nos. 4,912,266 and 4,912,267, issued Mar. 27, 1990; and 4,922,035 and 4,922,036, issued May 1, 1990, disclose decomposition of t-butyl hydroperoxide (TBHP) dissolved in t-butyl alcohol (TBA, t-butanol) over a metallophthalocyanine catalyst modified by imidazole and other modifiers. Sanderson et al., U.S. Pat. No. 4,992,602, issued Feb. 12, 1991, disclose partial oxidation of isobutane and distillation of the reaction product to obtain a fraction containing 80 to 90% of t-butyl hydroperoxide and 20 to 10% of t-butanol, dissolving that fraction in 3 to 10 parts by weight, based on the weight of the fraction, of benzene, and decomposing the hydroperoxide in the resulting solution with a phthalocyanine decomposition catalyst.

Taylor et al., U.S. Pat. No. 4,551,553, issued Nov. 5, 1985, disclose use of various metal acetylacetonate catalysts, including ruthenium, chromium, cobalt and manganese acetylacetonates, for decomposition of hydroperoxides in undried reaction systems. A catalyst comprising a combination of chromium and ruthenium acetylacetonates was found to have the highest reaction rate in such undried systems.

Lyons and Ellis, U.S. Pat. No. 5,120,886, issued Jun. 9, 1992, disclose and claim decomposition of hydroperoxides by contact with metal ligand catalysts of coordination complexes, including phthalocyanine ligands, in which hydrogen in the phthalocyanine molecule has been substituted with electron-withdrawing elements or groups, for example halogen or nitro or cyano groups. Other ligands than phthalocyanines can be used, for example porphyrins and others as subsequently disclosed.

In co-pending application, Ser. No. 08/223,090, filed Apr. 4, 1994, Bhinde et al. disclose and claim methods for decomposition of hydroperoxides catalyzed by metal organic ligand catalysts wherein the reaction mixture is dried. Suitable ligands for the method disclosed by Bhinde et al. include, but are not limited to, phthalocyanines, porphyrins, Schiff bases and acetylacetonates.

SUMMARY OF THE INVENTION

The invention comprises a method for decomposition of organic hydroperoxides to hydroxyl compounds such as alcohols which comprises drying a reaction mixture of an organic hydroperoxide in an organic solvent for the hydroperoxide such that said dried reaction mixture comprises approximately 1 weight percent or less of water, and contacting the dried reaction mixture with a metal organic ligand catalyst. Suitable catalysts include cobalt or ruthenium acetylacetonates, metalloporphyrins, metallophthalocyanines and others as subsequently disclosed. Reducing the water content of the reaction mixture to approximately 1 weight percent or less has been found to significantly promote the decomposition rate, compared with the decomposition rate obtained using a hydroperoxide solution which has not been dried to such a degree.

DESCRIPTION OF THE FIGURES

FIG. 3 is an approximate indication of the relative initial reaction rates as a function of water concentration.

FIGS. 4 and 5 together show the effect of water concentration on the decomposition of t-butyl hydroperoxide in t-butyl alcohol catalyzed by ruthenium acetylacetonate ($Ru(acac)_3$) in wet and dry systems, respectively, as measured by the amount of $O_2$ evolved (mmoles) over time (hours). FIG. 6 shows the decomposition of TBHP catalyzed by the combination of $Co(acac)_2$ and $Ru(acac)_3$ in a dried system.

DETAILED DESCRIPTION OF THE INVENTION

Figure 1:
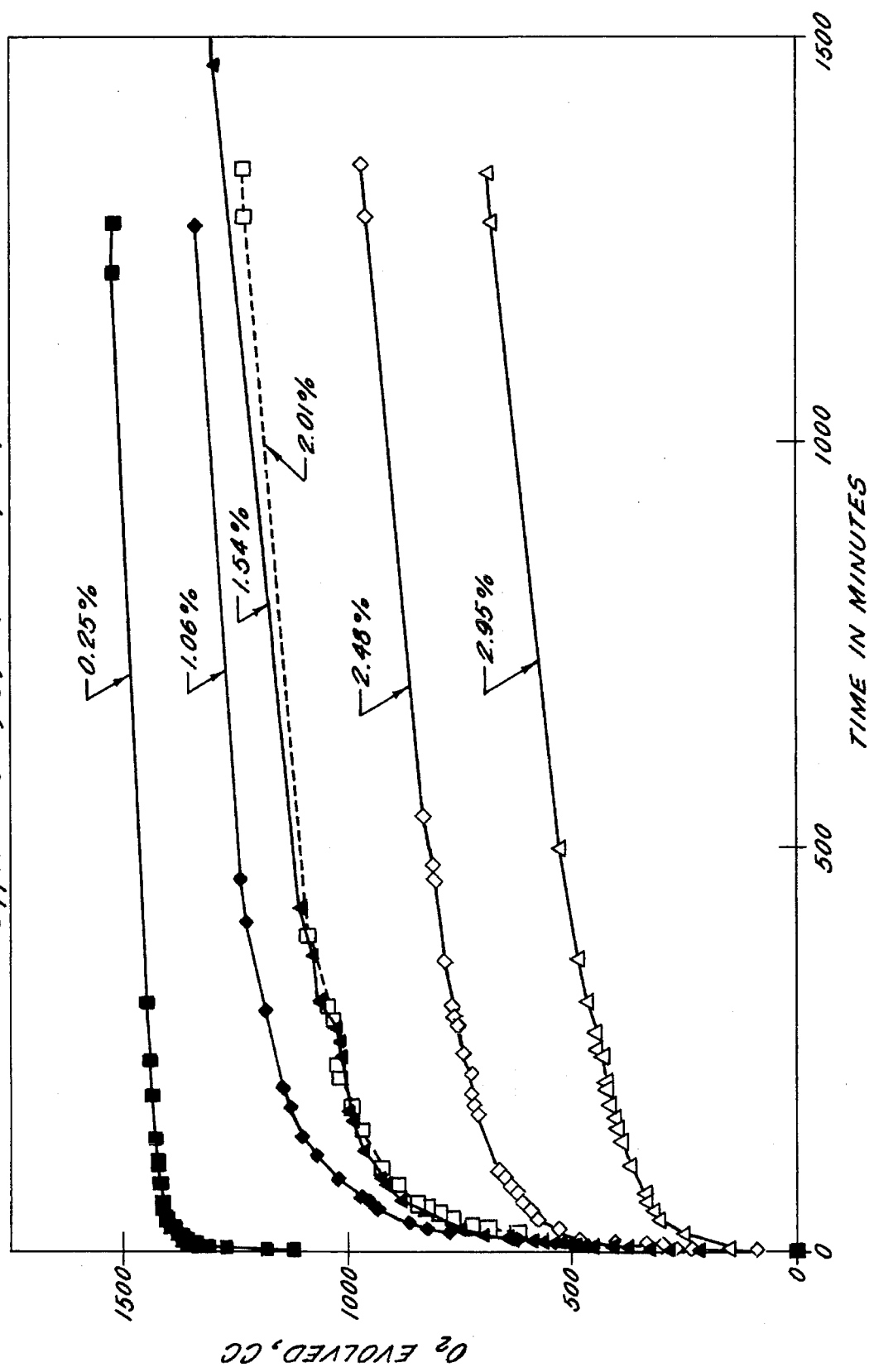
FIGS. 1 and 2 show the effect of water concentration on the decomposition of t-butyl hydroperoxide in t-butyl alcohol catalyzed by cobalt acetylacetonate ($Co(acac)_2$), as measured by the amount of $O_2$ evolved (cc) over time (min).

The invention comprises a method for decomposition of organic hydroperoxides to hydroxyl compounds such as alcohols which comprises drying a solution of an organic hydroperoxide in at least one organic solvent for the hydroperoxide such that said dried reaction mixture comprises approximately 1 weight percent or less of water, and contacting the dried reaction mixture with a metal organic ligand catalyst. Suitable catalysts include cobalt or ruthenium acetylacetonates, metalloporphyrins, metallo-phthalocyanines and others as subsequently disclosed. Reducing the water content of the reaction mixture to approximately 1 weight percent or less has been found to significantly promote the decomposition rate, compared with the decomposition rate obtained using a hydroperoxide solution which has not been dried to such a degree. The invention further comprises decomposing reaction mixtures which have been previously dried or which otherwise comprise approximately 1 wt. % or less of water.

"Drying" means reducing the water content of the hydroperoxide and/or the solvent. Thus, the hydroperoxide may be dried, then dissolved in the solvent, or the solvent may be dried and the hydroperoxide then dissolved in it, or a solution of hydroperoxide in the solvent may be dried, or dried hydroperoxide and dried solvent may be combined. Where a co-solvent is used as described below, the co-solvent may be dried together with or separately from the other components of the reaction mixture, in generally similar fashion. A drying step may also be applied to the solution comprising the catalyst, for example catalyst in acetone.

DRYING OF HYDROPEROXIDE AND/OR SOLVENT

The drying step in the method of the invention may be accomplished by any suitable means for removal of water from organic compounds, such as contact with granular solid drying agents, such as molecular sieves, alumina, silica gel, clays, $MgSO_4$ and the like, azeotropic distillation, contact with organic drying agents such as ethyl orthoformate, preferably regenerable organic drying agents such as diethyl acetals or ketals, for example dimethylacetal, diethylacetal, di t-butyl acetate, 2,2-dialkoxypropanes such as 2,2-dimethoxypropane and the like. Any substantial drying of the hydroperoxide and/or solvent or solvents which reduces the water content of the reaction mixture to approximately 1 weight percent or less is within the scope of the invention. Preferably, the water content is 0.5 wt. % or less, more preferably 0.25 wt. %, and still more preferably 0.1 wt. %. Generally, the greater the extent of the drying, up to total or substantially total drying, the greater the beneficial effect on the decomposition rate of the hydroperoxide.

USE OF CO-SOLVENT

In one embodiment of the invention, the solvent as previously disclosed, hereinafter sometimes referred to as the primary solvent, is used in conjunction with a co-solvent. Such co-solvent is a solvent different from the primary solvent, which may be added to the hydroperoxide and primary solvent to form a solution of hydroperoxide in the primary solvent and co-solvent. Ketones, such as acetone, methylethylketone, methyl-isobutylketone, cyclohexanone and the like, function effectively as co-solvents, resulting in increased rates of decomposition of hydroperoxides, as compared with the use of the primary solvent without a co-solvent, or as compared with the use of either the primary solvent or the co-solvent alone.

Various types of solvents, for example ketones, are capable of functioning either as primary solvents or as co-solvents. When two solvents are used in conjunction, with one solvent present in larger concentration than the other, the one used in the larger concentration is conveniently considered the primary solvent and the other the co-solvent. If they are present in equal amounts, either may be considered the primary solvent. Typically the proportions of primary solvent and co-solvent will be in the range from 1 to 100 parts by volume of co-solvent per 100 parts of primary solvent, but this depends upon the solubility characteristics of a particular pair of solvents in relation to a particular hydroperoxide, and the optimum proportions may be determined by a person skilled in the art in the light of the present specification. The use of more than two solvents is within the scope of the invention.

HYDROPEROXIDES

Hydroperoxides for decomposition according to the invention include compounds having the formula ROOH where R is an organic radical, typically a straight or branched chain alkyl group or cycloalkyl group containing 2 to 15 carbon atoms, an aryl group such as a monocyclic or polycyclic group in which the cyclic groups may optionally be substituted with one or more substituents inert to the decomposition reaction, such as alkyl or alkoxy, containing 1 to 7 carbon atoms, nitro, carboxyl or carboxyl ester containing up to 15 carbon atoms and a halogen atom such as chloride, bromide or an alkylaryl group in which the alkyl chain contains 1 to 15 carbon atoms and the aryl group is as above described. Preferably, R is an alkyl or cycloalkyl group containing 4 to 12 carbon atoms or an alkylaryl group in which the aromatic moiety is phenyl and the alkyl group is straight or branched chain alkyl or cycloalkyl containing up to 6 carbon atoms.

Examples of hydroperoxides for decomposition according to the invention are t-butyl hydroperoxide, isoamyl hydroperoxide, t-amylhydroperoxide, cyclohexyl hydroperoxide, alpha- and beta-ethylbenzene hydroperoxide, cumyl hydroperoxide, phenethyl hydroperoxide and cyclohexylphenyl hydroperoxide; phenethyl hydroperoxide and cumyl hydroperoxide are converted to phenethyl alcohol and cumyl alcohol respectively. Preferred are the alkyl hydroperoxides such as t-butyl hydroperoxide, isoamyl hydroperoxide, and the like, and the cycloalkyl hydroperoxides such as cyclohexyl hydroperoxide, methylcyclohexyl hydroperoxide, and the like.

HYDROPEROXIDE DECOMPOSITION CATALYSTS

Hydroperoxide decomposition catalysts for use according to the invention comprise the transition metal complexes of ligands such as phthalocyanines, porphyrins, porphenes, porphycenes, acetylacetonates, 1,3-bis(arylimino)isoindolines such as "BPI", Schiff bases such as salen, saleph and the like, halogenated mono-, bi-, tri- and tetradentate ligand systems such as propanates, butyrates, benzoates, naphthenates, stearates, bipyridines, terpyridines, phenanthrolines, dithiocarbamates, xanthates, salicylaldimines, cyclam, dioxycyclams, pyrazolyl borates and tetraazamacrocycles such as tetramethyltetraazadibenzocycloheptadecane. Suitable metals for the catalysts useful in the present invention include chromium, manganese, iron, cobalt and ruthenium. In one embodiment of the invention, preferred are the ligands having the hydrogen atoms of the molecule substantially completely replaced with electron-withdrawing atoms or groups such as halogen, nitro, cyano, halocarbyl, nitrocarbyl, cyanocarbyl and the like. The catalysts useful in the process of the present invention may be produced by conventional methods known in the art. See, Bhinde et al., U.S. Ser. No. 08/223,090, which is incorporated by reference herein; and the references cited herein.

Figure 2:
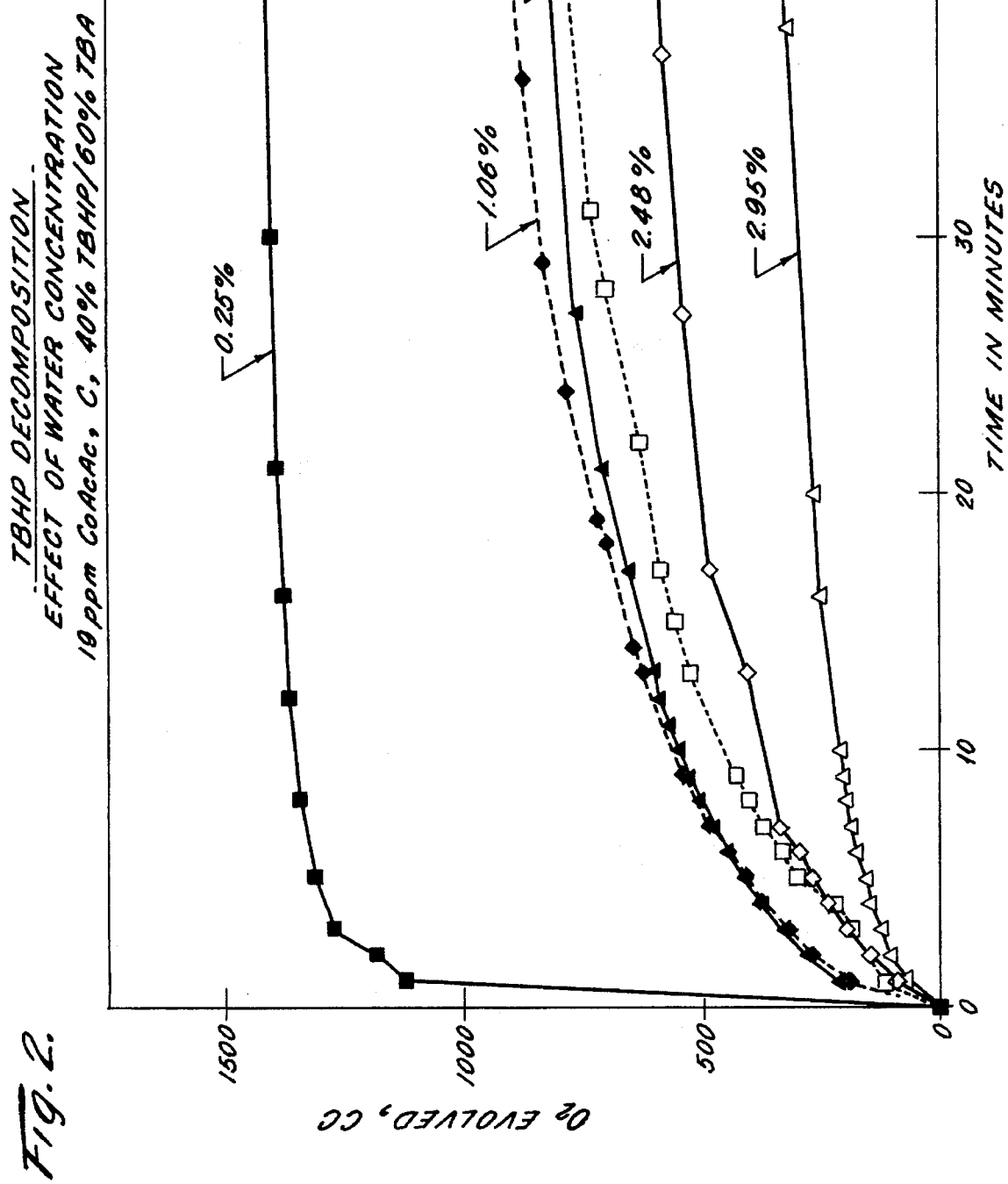
Figure 3:
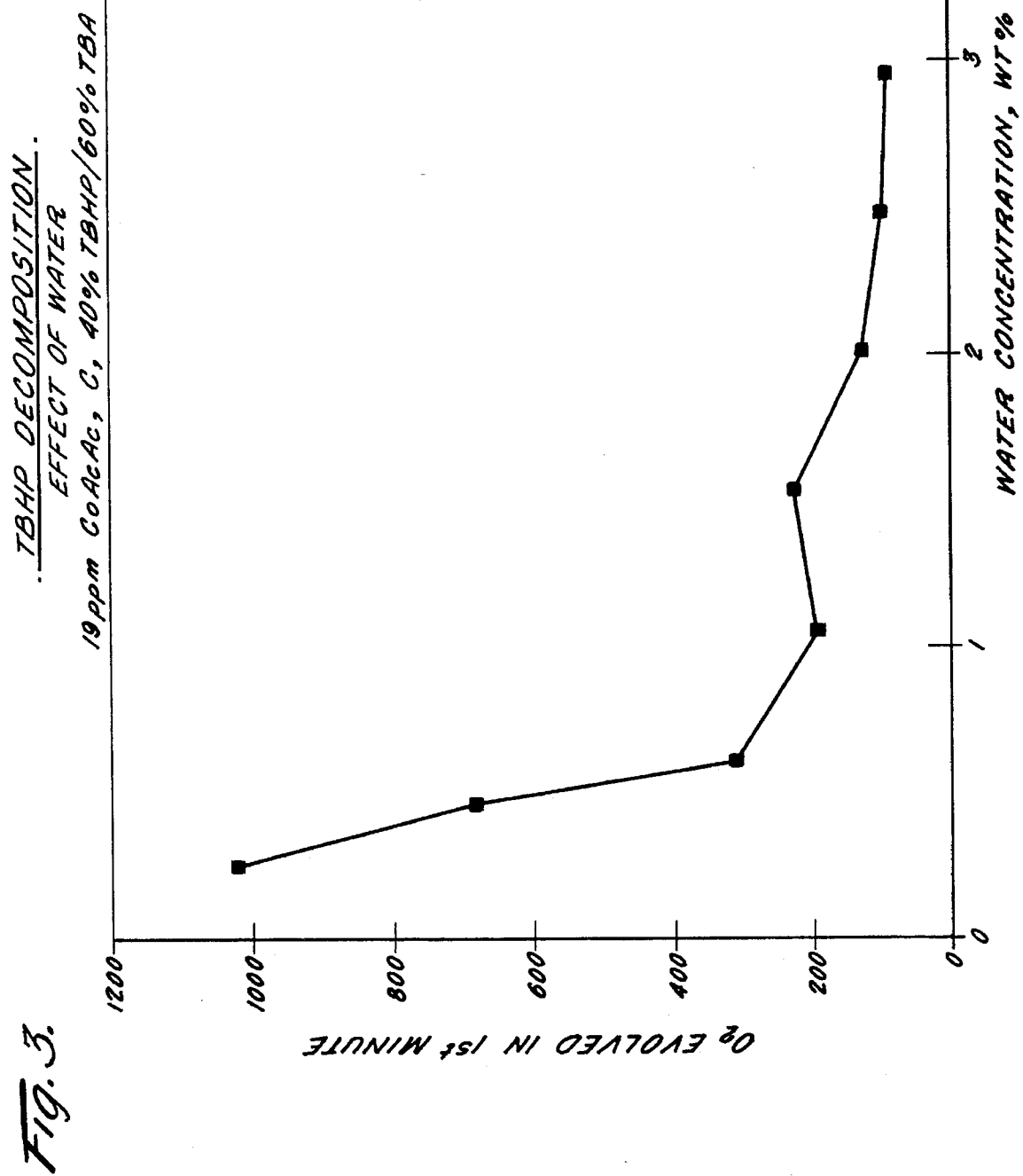
FIG. 3 shows the same effect as measured by the $O_2$ evolved in the first minute of the reaction as a function of the water concentration (in weight percent) in the reaction mixture.

As noted above, the process of the present invention results in a surprising and unexpectedly great increase in the decomposition rate of organic hydroperoxides. An advantage of the present invention is that inexpensive and readily available compositions, which previously were completely or essentially inactive as catalysts, exhibit enhanced activity when utilized in the present invention. Examples of such catalysts are unsubstituted metallophthalocyanines and the metal acetylacetonates, such as cobalt acetylacetonate ($Co(acac)_2$) and ruthenium acetylacetonate ($Ru(acac)_3$). For example, $Co(acac)_2$ has no catalytic activity for decomposition of t-butyl hydroperoxide when the reaction system is contaminated with 5 wt. % water. In contrast, when there is less than 1 wt. % water in the reaction mixture, the same composition is a highly active catalyst. FIGS. 1 to 3 illustrate this result.

In one embodiment of the invention, the catalyst is a mixture of metallo-phthalocyanine and metal acetylacetonate, for example, iron phthalocyanine (FePc) and $Co(acac)_2$. In another, the catalyst is a mixture of ruthenium acetylacetonate and cobalt acetylacetonate; the former appears to produce a higher overall conversion rate while the latter exhibits a shorter induction period and greater initial reaction rate. The weight ratio of $Ru(acac)_3$ to $Co(acac)_2$ may be from 0.01:1 to 100:1 (Ru:Co), preferably 0.1:1 to 10:1, more preferably 0.1:1 to 1:1. The relative proportion of $Co(acac)_2$ to $Ru(acac)_3$ may be modified to balance reaction rate, conversion rate and catalyst cost. Effecting the desired balance is within the ability of the skilled practitioner in the art.

PREPARATION OF REACTION MIXTURE

The decomposition catalyst may either be dissolved or slurried in the reaction mixture; i.e., in the primary solvent, or if a co-solvent is used, in the co-solvent, or a combination thereof. The effectiveness of the catalyst may be improved by stirring the catalyst in the solvent or co-solvent for at least 24, and up to 168 or more hours. This time can be reduced by heating the slurry, sonication or other devices known to accelerate both solution and dispersion phenomena. The catalyst slurry may be mixed with a solution of the hydroperoxide in the primary solvent, and the resulting mixture or solution subjected to the reaction temperature as subsequently described.

SOLVENTS AND DECOMPOSITION CONDITIONS

The decomposition of hydroperoxides according to the invention is typically carried out in a solution of the hydroperoxide in the solvent or solvent mixture. The solution preferably contains from about 5 to about 50 wt. % of hydroperoxide, but may also contain less, for instance 1 wt. % of hydroperoxide. Suitable solvents or co-solvents include benzene, chlorobenzene, o-dichlorobenzene, acetonitrile, benzonitrile, hydroxyl or carbonyl compounds such as alcohols or ketones and the like. A useful solvent is the alcohol formed by decomposition of the hydroperoxide, for example TBA formed by decomposition of TBHP. Any suitable temperature and pressure may be used. Preferably the temperature is in the range from about 25° to about 150° C., and the total pressure from 0 to 500 psig; preferably, the partial pressure of the oxygen in the solution is not more than about 50 psig. The time of reaction may be relatively short, in view of the rapid reaction rate with the catalysts employed according to the invention, and will typically be in the range from about 0.1 to about 5 hours. The drying of the reaction mixture according to the invention may be effected before contacting the hydroperoxide and solvent or solvents with the decomposition catalyst, or it may be effected in situ in the decomposition reaction.

DRYING AND USE OF CO-SOLVENT

The drying of the reaction mixture according to the invention is applicable to reaction mixtures which contain one solvent, and to reaction mixtures which contain a primary solvent and one or more co-solvents. The use of one or more co-solvents according to the invention is applicable to reaction mixtures which are dried, and to reaction mixtures which are not dried. In a preferred embodiment, the reaction mixture is dried and contains one or more co-solvents.

INTEGRATION OF OXIDATION AND HYDROPEROXIDE DECOMPOSITION

The hydroperoxide which is decomposed according to the invention may have been obtained from any source. Where the hydroperoxide has been prepared by a noncatalytic or catalytic partial oxidation of hydrocarbons, the decomposition of the hydroperoxide may conveniently be integrated with the previous oxidation. The product mixture from the oxidation typically contains unreacted hydrocarbon, hydroperoxide and alcohol products of the partial oxidation, and water, and is typically fractionated to obtain a fraction comprising a water-containing solution of hydroperoxide in the alcohol product of the oxidation. In the integrated operation, the water-containing oxidation product or a water-containing fraction thereof, is passed to a drying operation wherein the water content is reduced. The product of the drying operation is passed to the decomposition of hydroperoxide according to the invention. The use of a drier unit prior to the hydroperoxide decomposition (HPD) unit allows for a substantial increase in HPD reactor throughput due to the increased reaction rate of the process of the invention, possibly as much as an order of magnitude or more. Alternatively, the drying operation may be carried out in the decomposition reactor itself, concurrently with the decomposition, rather than in a separate, prior step.

COMMERCIAL PRODUCTION OF t-BUTANOL

In the commercial noncatalytic production of t-butanol ("TBA") by partial oxidation of isobutane, a mixture of TBA and TBHP is typically obtained as reaction product. The TBHP is often reacted in a second step with an olefin to produce an alkylene oxide and TBA as products. The invention provides additional options in connection with such operation which may be advantageous in some cases. Thus, for example, the partial oxidation may be conducted either catalytically or noncatalytically to maximize TBHP production relative to TBA production, and the method of the invention used to convert the TBHP produced to TBA in a manner to maximize the overall production of TBA independently of any other product.

DRIED HYDROPEROXIDE AND ORGANIC SOLVENT COMPOSITIONS

Related to the invention are compositions of matter, useful in the methods of the invention, which comprise solutions of an organic hydroperoxide in an organic solvent, prepared by:

(a) drying the hydroperoxide to obtain a dried hydroperoxide and mixing the dried hydroperoxide with the dried or undried solvent, (b) drying the solvent and mixing the dried solvent with the dried or undried hydroperoxide, (c) drying a mixture of the hydroperoxide and the solvent, or (d) drying a product mixture from the partial oxidation of alkane that comprises hydroperoxide together with other by-products.

Preferably, the hydroperoxide-solvent or hydroperoxide-solvent-cosolvent composition of the invention contains less than 50%, and more preferably less than 25%, of the water in the corresponding undried composition, that is, the composition consisting of the same relative portions of the same components in their undried state. These compositions also preferably contain approximately 1 weight percent or less, preferably 0.5 wt. % or less, more preferably 0.1 wt. % or less, and still more preferably 0.1 wt. % or less of water. In contrast, typical commercial feeds may contain 2 to 5 wt. % or more of water. For example, where the undried composition contains 2 wt. % water, and the dried composition contains 0.05 wt. % water, the dried composition contains (0.05/2)×100, or 2.5%, of the water in the undried composition.

EXAMPLES

The following examples illustrate the invention.

Examples 1 through 5

Table I shows the effect of drying on the decomposition of t-butyl hydroperoxide (TBHP), solubilized in t-butyl alcohol (TBA), catalyzed by Co(acac)$_2$ at 80° C. and 0 psig. TBHP was decomposed in Examples 1 to 4 using Co(acac)$_2$, and the effect of drying was determined by varying the water level in the runs from 4.3 wt. % ("wet" TBHP) to 1.2 and 1.1 wt. % ("1× dried" TBHP) to 0.1 wt. % ("2× dried" TBHP). The procedure used was as described in footnotes 1, 2 and 3 to Table I. The percent conversion of TBHP was measured after 60 minutes. In Example 5, the decomposition reaction was run with no catalyst.

The data under the heading "% Conv of TBHP" in Table I indicate the relative activity of the runs. The conversion of TBHP increased from 46.4% for the wet system to 90.3% for the twice dried system with 0.1 wt. % water. Comparison of Examples 1 through 4 shows that drying of the reaction mixture significantly increased the conversion of TBHP. The results from Example 5 (39.0% conversion with no catalyst) highlight the poor activity of Co(acac)$_2$ in a wet system (see, Example 1).

TABLE I

TBHP Decomposition Catalyzed by Co(acac)$_2$ at 80° C. Effect of Drying TBHP

| Example No. | Catalyst Conc (ppm) | Water in Charge (wt %) | Time (min) | Pressure (psig) | % Conv. of TBHP |
|---|---|---|---|---|---|
| 1[1] | 89 | 4.3 (wet) | 60 | 0 | 46.4 |
| 2 | 89 | 1.2 (1× dried) | 60 | 0 | 88.2 |
| 3 | 89 | 0.1 (2× dried) | 60 | 0 | 90.3 |
| 4[2] | 83 | 1.1 (1× dried) | 60 | 0 | 77.3 |
| 5[3] | 0 | 1.1 (1× dried) | 60 | 0 | 39.0 |

[1]For Examples 1, 2, and 3: 5.4 g TBHP + 7.2 g dried TBA in stainless steel reactor; purge with N$_2$; heat and stabilize at 80° C.; add 4 aliquots of catalyst solution (674 ppm in dried TBA) at 0, 7, 14 and 21 minutes into the run.
[2]Same as "1", but the reactor charge contains 1 g dry acetone.
[3]Same as "1", but the reactor charge contains 1 g dry acetone, and no catalyst.

Examples 6 through 12

Table II shows the effect of drying on the decomposition of t-butyl hydroperoxide (TBHP), solubilized in t-butyl alcohol (TBA) and acetone, catalyzed by iron phthalocyanine (FePc) at 80° C. and 0 psig. TBHP was decomposed in Examples 6 to 10 using FePc, and the effect of drying was determined by varying the water level in the runs from 3.8 wt. % ("wet" TBHP) to 1.8 wt. % ("1× dried" TBHP) to 0.05 wt. % ("2× dried" TBHP). In Example 11, water was added to a twice dried reaction mixture to yield 0.33 wt. % water. In Example 12, the reaction was run with "wet" TBHP with 2 g of activated molecular sieve drying agent in the reaction system.

TABLE II

TBHP Decomposition Catalyzed by FePc at 80° C. Effect of Drying TBHP

| Example No. | Catalyst Conc. (ppm) | Water in Charge (wt. %) | Pressure (psig) | % Conv. of TBHP | Remarks |
|---|---|---|---|---|---|
| 6 | 9 | 3.8 | 0 | 23.0 | wet TBHP |
| 7 | 9 | 3.8 | 0 | 19.9 | wet TBHP |
| 8 | 9 | 1.8 | 0 | 56.8 | 1× dried TBHP |
| 9 | 9 | 1.8 | 0 | 53.5 | 1× dried TBHP |
| 10 | 9 | 0.05 | 0 | 63.8 | 2× dried TBHP |
| 11 | 9 | 0.33 | 0 | 61.9 | 2× dried |
| 12 | 9 | 3.8 | 0 | 40.5 | TBHP + 0.04 g water wet + 2 g 3A mol. sieve added |

5.4 g TBHP + 7.2 g dried TBA + 1 g dried acetone in stainless steel reactor; purge with N$_2$; heat and stabilize at 80° C.; inject 0.6 ml catalyst solution (674 ppm in dried acetone) at time 0. Run for 60 min; cool down and analyze product.

The procedure used was as described in the footnote to Table II. The percent conversion of TBHP was measured after 60 minutes. The results in Table II further illustrate the positive effect of drying the reaction mixture on the percent conversion of TBHP. Conversion after 1 hour with the catalyst is approximately three times greater in the twice-dried system as compared to the wet system.

The results for the decomposition of TBHP catalyzed by Co(acac)$_2$ and the effect of drying on that reaction are further illustrated in FIGS. 1 through 6. FIGS. 1 and 2 represent hydroperoxide decomposition by the amount of O$_2$ (in cc's) evolved in the reaction plotted against the reaction time (in minutes). They dramatically show that as water is removed from the reaction mixture, Co(acac)$_2$ becomes an increasingly superior decomposition catalyst. It has been found that Co(acac)$_2$ has little or no catalytic activity under the reaction conditions described herein when the TBHP feed is contaminated with approximately 5 wt. % water (results not shown). In contrast, FIGS. 1 and 2 show that drying to approximately 1 wt. % or lower of water results in a very active catalyst. The data in Table III further evidence this high catalytic activity of Co(acac)$_2$ for decomposition in dried conditions.

FIG. 3 shows the dramatic increase in the decomposition rate for the Co(acac)$_2$-catalyzed decomposition of TBHP in TBA as water is removed from the reaction mixture. The Figure plots the O$_2$ evolved in the first minute of the reaction against the water concentration in the reaction mixture. The data show that the rate begins to rise rapidly as the water concentration is decreased below 1 wt. %. In fact, the initial reaction rate at 0.25 wt. % water in feed is five times greater than at 1 wt. % water in feed.

FIGS. 4 and 5 illustrate the effect of drying on TBHP decomposition catalyzed by Ru(acac)$_3$ by showing the results in wet and dried systems, respectively. TBHP was solubilized in TBA; the reaction was run at 80° C.; and activity was measured as a function of O$_2$ evolved (in mmoles) and plotted against reaction time (in hours). In FIG. 5, it can be seen that, after a brief induction period, the decomposition reaction was observed to proceed extremely rapidly. The reaction was 98% complete after one hour.

FIG. 6 illustrates the further positive effect that occurs when the combination of Co(acac)$_2$ and Ru(acac)$_3$ is used as the catalyst for TBHP decomposition in a dried system.

TABLE III

Effect of Added Water on Co(acac)$_2$ Catalyzed Conversion of TBHP to TBA

| Water wt. % | O$_2$ Evolved, cc, after time period, min | | | | | | TBHP Conv. (%) | TBA (Mol %) |
|---|---|---|---|---|---|---|---|---|
| | 5 | 7 | 20 | 30 | 60 | 1440 | | |
| 0.25 | 1310 | 1330 | 1380 | 1390 | 1410 | 1440 | 95 | 96 |
| 1.06 | 410 | 480 | 720 | 820 | 950 | 1320 | 85 | 92 |
| 1.54 | 420 | 480 | 690 | 770 | 870 | 1280 | 78 | 92 |
| 2.01 | 300 | 370 | 610 | 720 | 840 | 1085 | 74 | 88 |
| 2.48 | 270 | 340 | 500 | 540 | 610 | 950 | 59 | 80 |
| 2.95 | 160 | 200 | 260 | 280 | 320 | 670 | 30 | 71 |
| 4.11 | -NR- | -NR- | -NR- | -NR- | -NR- | -NR- | — | — |

The catalyst, 0.6 g, was added to a stirred solution of TBHP (13.9 g), TBA (18.1 g), and water (added to the concentration designated in the Table) at 80° C. Oxygen evolution was monitored manometrically over time. The liquid phase was analyzed periodically by standardized GLPC and a final analysis done at 24 hours — results reported in the Table.

Example 13

A solution from a concentrated cyclohexane oxidate comprising cyclohexyl hydroperoxide (10%), cyclohexanone (58%) and cyclohexanol (31%) and small amounts of other organic materials including cyclohexane is dried for 72 hours over freshly activated molecular sieve. The dried reaction mixture is then catalytically decomposed using Co(acac)$_2$. The rate of decomposition of the dried reaction mixture is more than twice that of an identical undried sample.

Example 14

A concentrated cyclohexane solution comprising 10.5% cyclohexyl hydroperoxide, 2.5% cyclohexanol, 1% cyclohexanone and 3.5% other oxidation products is generated by non-catalytic oxidation of cyclohexane in a passivated reactor. The reaction mixture is dried over 3 A molecular sieves. The dried reaction mixture is then catalytically decomposed using Co(acac)$_2$. Decomposition of the hydroperoxide in this mixture occurs far more rapidly when the mixture is thoroughly dried over 3 A molecular sieves than when the undried material is used.

The invention claimed is:

1. Method for decomposing organic hydroperoxides which comprises drying a reaction mixture comprising an organic hydroperoxide, an organic solvent for said hydroperoxide, and water, thereby to obtain a dried reaction mixture and contacting said dried reaction mixture with a metal organic ligand catalyst for said decomposing, the improvement which comprises drying said reaction mixture such that said water comprises approximately 1 weight percent or less of said dried reaction mixture.

2. Method according to claim 1 wherein said water comprises approximately 0.5 weight percent or less of said dried reaction mixture.

3. Method according to claim 2 wherein said water comprises approximately 0.25 weight percent or less of said dried reaction mixture.

4. Method according to claim 3 wherein said water comprises approximately 0.1 weight percent or less of said dried reaction mixture.

5. Method according to claim 1 wherein said metal organic ligand catalyst comprises ligand selected from the group consisting of phthalocyanines, other tetraazamacrocycles, porphyrins, porphenes, porphycenes, 1,3-bis(arylimino)-isoindolines, acetylacetonates, Schiff bases, halogenated mono-, bi-, tri- and tetradentate ligand systems, or combinations thereof.

6. Method according to claim 5 wherein said metal is selected from the group consisting of chromium, manganese, iron, ruthenium and cobalt.

7. Method according to claim 6 wherein said catalyst comprises metal acetylacetonate or mixtures thereof.

8. Method according to claim 7 wherein said catalyst comprises cobalt acetylacetonate.

9. Method according to claim 7 wherein said catalyst comprises ruthenium acetylacetonate.

10. Method according to claim 7 wherein said catalyst comprises a mixture of ruthenium acetylacetonate and cobalt acetylacetonate.

11. Method according to claim 5 wherein said catalyst comprises a metallophthalocyanine.

12. Method according to claim 11 wherein hydrogen atoms of said phthalocyanine have been replaced with electron-withdrawing atoms or groups.

13. Method according to claim 12 wherein said electron-withdrawing atoms or groups are selected from selected from the group consisting of halogen, cyano, nitro and halocarbyl.

14. Method according to claim 13 wherein said catalyst comprises a metallohalophthalocyanine.

15. Method according to claim 14 wherein said catalyst comprises a metalloperhalophthalocyanine.

16. Method according to claim 5 wherein said catalyst comprises a mixture of metallophthalocyanine and metal acetylacetonate.

17. Method according to claim 16 wherein said catalyst comprises a mixture of iron phthalocyanine and cobalt acetylacetonate.

18. Method according to claim 5 wherein said catalyst comprises a metalloporphyrin.

19. Method according to claim 18 wherein hydrogen atoms of said porphyrin have been replaced with electron-withdrawing atoms or groups.

20. Method according to claim 19 wherein said electron-withdrawing atoms or groups are selected from selected from the group consisting of halogen, cyano, nitro and halocarbyl.

21. Method according to claim 20 wherein said catalyst comprises a metallohaloporphyrin.

22. Method according to claim 21 wherein said catalyst comprises a metalloperhaloporphyrin.

23. Method according to claim 1 wherein said hydroperoxide comprises an alkylhydroperoxide.

24. Method according to claim 23 wherein said hydroperoxide comprises t-butyl hydroperoxide.

25. Method according to claim 1 wherein said solvent is a hydroxyl-containing organic compound.

26. Method according to claim 25 wherein said solvent comprises t-butanol.

27. Method according to claim 1 wherein said hydroperoxide comprises cyclohexyl hydroperoxide.

28. Method according to claim 1 wherein said reaction mixture additionally comprises an organic co-solvent for said hydroperoxide.

29. Method according to claim 28 wherein said co-solvent comprises a ketone.

30. Method according to claim 1 wherein said contacting occurs at a temperature in the range from about 25° C. to about 150° C. and at a total pressure not greater than about 500 psig.

31. Method according to claim 1 wherein said drying of said reaction mixture is in the absence of said catalyst.

32. Method according to claim 1 wherein said drying of said reaction mixture is in the presence of said catalyst.

33. Method according to claim 32 wherein said hydroperoxide, said solvent, said water and said catalyst are contacted with a granular solid drying agent, thereby to remove water from said reaction mixture and decompose said hydroperoxide.

34. Method for decomposing organic hydroperoxides which comprises contacting a reaction mixture comprising an organic hydroperoxide, at least one organic solvent for said hydroperoxide and approximately 1 weight percent or less of water with a metal organic ligand catalyst for said decomposing.

35. Method according to claim 34 wherein said water comprises approximately 0.5 weight percent or less of said dried reaction mixture.

36. Method according to claim 35 wherein said water comprises approximately 0.25 weight percent or less of said dried reaction mixture.

37. Method according to claim 36 wherein said water comprises approximately 0.1 weight percent or less of said dried reaction mixture.

* * * * *